US012782342B2

(12) United States Patent
Carding et al.

(10) Patent No.: US 12,782,342 B2
(45) Date of Patent: Nov. 3, 2026

(54) METHODS AND COMPOSITIONS UTILISING VITAMIN B12 BINDING

(71) Applicant: Quadram Institute Bioscience, Norwich Norfolk (GB)

(72) Inventors: Simon Carding, Norwich Norfolk (GB); Rokas Juodeikis, Norwich Norfolk (GB); Martin James Warren, Norwich Norfolk (GB)

(73) Assignee: Quadram Institute Bioscience, Norwich (GB)

(*) Notice: Subject to any disclaimer, the term of this patent is extended or adjusted under 35 U.S.C. 154(b) by 582 days.

(21) Appl. No.: 18/039,132

(22) PCT Filed: Nov. 29, 2021

(86) PCT No.: PCT/GB2021/053106
§ 371 (c)(1),
(2) Date: May 26, 2023

(87) PCT Pub. No.: WO2022/112795
PCT Pub. Date: Jun. 2, 2022

(65) Prior Publication Data

US 2024/0053332 A1 Feb. 15, 2024

(30) Foreign Application Priority Data

Nov. 27, 2020 (GB) .................................... 2018713

(51) Int. Cl.
*G01N 33/532* (2006.01)
*G01N 33/82* (2006.01)

(52) U.S. Cl.
CPC .......... *G01N 33/532* (2013.01); *G01N 33/82* (2013.01)

(58) Field of Classification Search
CPC ............................ G01N 33/532; G01N 33/82
See application file for complete search history.

(56) References Cited

U.S. PATENT DOCUMENTS

| | | | |
|---|---|---|---|
| 4,465,775 | A | 8/1984 | Houts |
| 5,574,018 | A | 11/1996 | Habberfield et al. |

FOREIGN PATENT DOCUMENTS

| | | | |
|---|---|---|---|
| EP | 1377220 | A1 | 1/2004 |
| WO | 9808859 | A1 | 3/1998 |
| WO | 0130967 | A2 | 5/2001 |

OTHER PUBLICATIONS

Wexler et al. Human gut Bacteroides capture vitamin B12 via cell surface-exposed lipoproteins. Microbiology and Infectious Disease (Sep. 18, 2018).*

Wexler et al, “Human gut bacteroides capture vitamin B12 via cell surface-exposed lipoproteins”, https://www.ncbi.nlm.nih.giv/pmc/articles/PMC6143338/, Sep. 18, 2018, Publisher: eLife; SP55892425.

* cited by examiner

*Primary Examiner* — Gailene Gabel
(74) *Attorney, Agent, or Firm* — GableGotwals

(57) ABSTRACT

A composition for labelling, detection, immobilisation and/or isolation of at least one target molecule. The composition including a non-covalent affinity, coupling or binding between vitamin B12 binding protein BtuG2 and at least one bond formed between the vitamin B12 and the target molecule. The interaction between BtuG2 and vitamin B12 enables the labelling, immobilisation, isolation and/or detection of the target molecule.

18 Claims, 3 Drawing Sheets

METHODS AND COMPOSITIONS UTILISING VITAMIN B12 BINDING

CROSS-REFERENCE TO RELATED APPLICATIONS

This United States application is the National Phase of PCT Application No. PCT/GB2021/053106 filed 29 Nov. 2021, which claims priority to British Patent Application No. 2018713.4 filed 27 Nov. 2020, each of which is incorporated herein by reference.

The present invention relates to the attachment of vitamin $B_{12}$, cobalamin, to proteins, peptides, nucleic acid and other molecules.

The present invention provides compounds, methods, and kits for attaching vitamin $B_{12}$ to molecules and linking via vitamin $B_{12}$ binding agents, and refers exclusively to the conjugation of $B_{12}$ to fluorescent proteins using said binding agent, the person skilled in the art will appreciate that the present invention is not limited to such an fluorescent protein attachment and the affinity can be utilised in a wide range of biotechnological application including labelling and isolation of molecules of interest, as well as diagnostics, probes, affinity matrices and medical devices.

Strong binding partners have the potential to be used as powerful tools in the biosciences, where they can be exploited as probes and affinity matrices. In the case of avidin/biotin this progress stemmed from the ability to chemically modify biotin to allow its attachment to antibodies and other biomolecules.

Most chemical biotinylation reagents consist of a reactive group attached via a linker to the valeric acid side chain of biotin, thereby allowing various conjugation chemistries to yield nonspecific biotinylation of amines, carboxylates, sulphydryls and carbohydrates.

It is therefore an aim of the present invention to provide an improved conjugation chemistries utilising vitamin $B_{12}$.

In a first aspect of the invention there is provided a composition for labelling, detection, immobilisation and/or isolation of at least one target molecule, said composition including a non-covalent affinity, coupling or binding between vitamin $B_{12}$ binding protein BtuG2 and at least one bond formed between the vitamin $B_{12}$ and the target molecule in use, said interaction between BtuG2 and vitamin $B_{12}$ enabling the labelling, immobilisation, isolation and/or detection of the target molecule.

Preferably the target molecule is a biological molecule. Typically the target biological molecule is a peptide, protein and/or antibody.

In one embodiment the bond between the vitamin $B_{12}$ and the target molecule is a covalent bond. Typically the target biological molecule is connected via a bond to the primary hydroxyl site of the ribose moiety of vitamin B12.

Many proteins and peptides can be conjugated to vitamin $B_{12}$. For example, U.S. Pat. No. 5,574,018 teaches vitamin $B_{12}$ conjugated to erythropoietin, granulocyte colony stimulating factor and consensus interferon through covalent binding at the primary hydroxyl site of the ribose moiety of the vitamin $B_{12}$.

Conjugates of other bioactive agents and vitamin $B_{12}$ are taught by Grissom et al. (WO 01/30967 & WO 98/08859). Grissom et al. teach covalent attachment of cancer treatment drugs to the cobalt atom of vitamin $B_{12}$.

In one embodiment vitamin $B_{12}$ is not directly linked to the target molecule. Typically the indirect linkage is via a bridging molecule, linking elements or particles.

Typically the target biological molecule is a protein, peptide, nucleic acid, antibody and/or other biological molecule.

In one embodiment vitamin $B_{12}$ is conjugated to one or more fluorescent protein target molecules. Typically the florescent proteins are GFP, Citrin and/or mCherry.

Typically the conjugated proteins then bind to BtuG2 via vitamin $B_{12}$. The $B_{12}$-BtuG2 couple holding large potential for use in a wide range of biotechnological applications.

In one embodiment vitamin $B_{12}$ is modified or attached to the target molecule by attachment to the 5' hydroxyl of the ribose of the lower nucleotide loop of cobalamin. Typically it is therefore possible to couple vitamin $B_{12}$ to a range of proteins or matrices, effectively mimicking the modifications that can be achieved on biotin.

In one embodiment the vitamin $B_{12}$ is modified or attached to the target molecule by attachment to the secondary alcohol on cobinamide.

In one embodiment a linker compound is used to modify vitamin $B_{12}$ with a linker compound or element to allow $B_{12}$ conjugation to a wider range of target molecules and proteins.

In one embodiment the linker compound is succinyl anhydride and the associated chemistry attaching the protein target shown below:

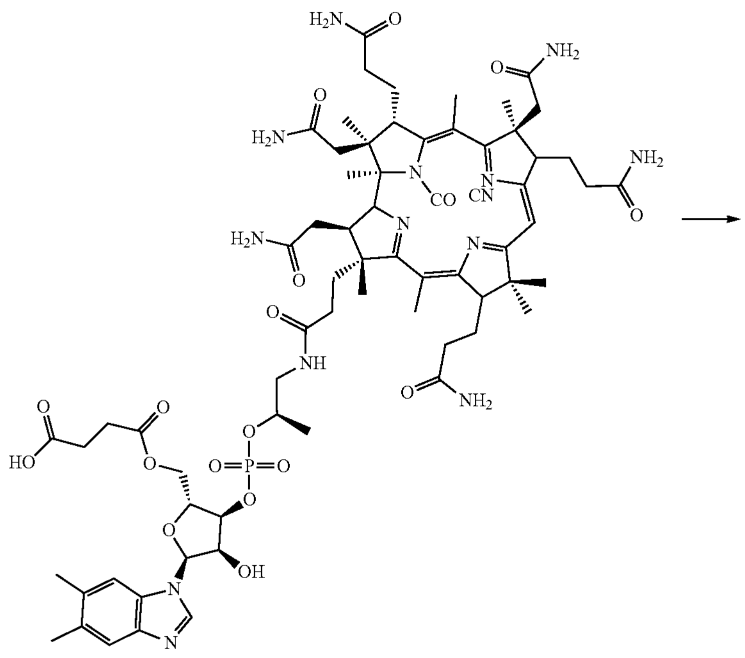
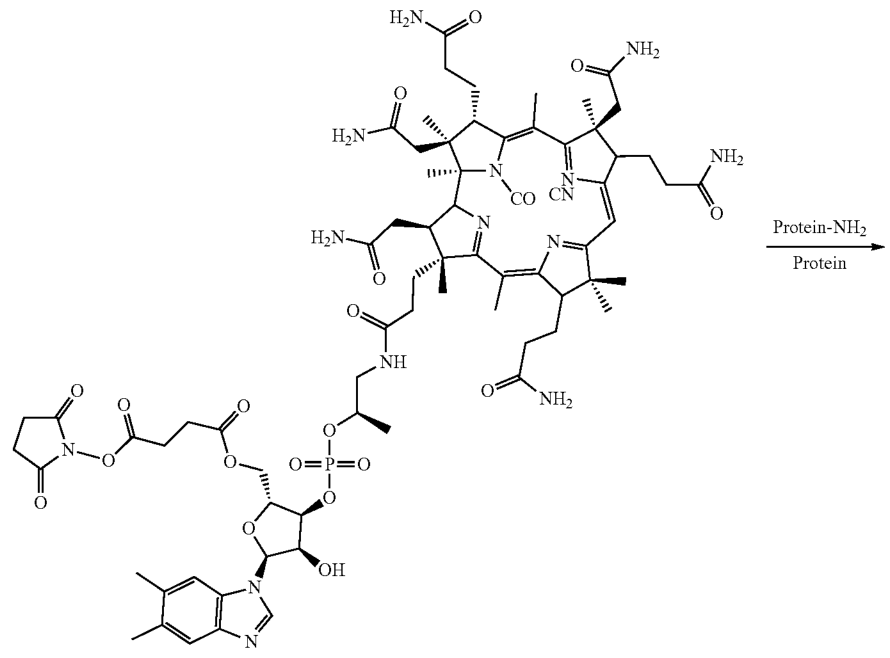
Protein-NH2
Protein

-continued

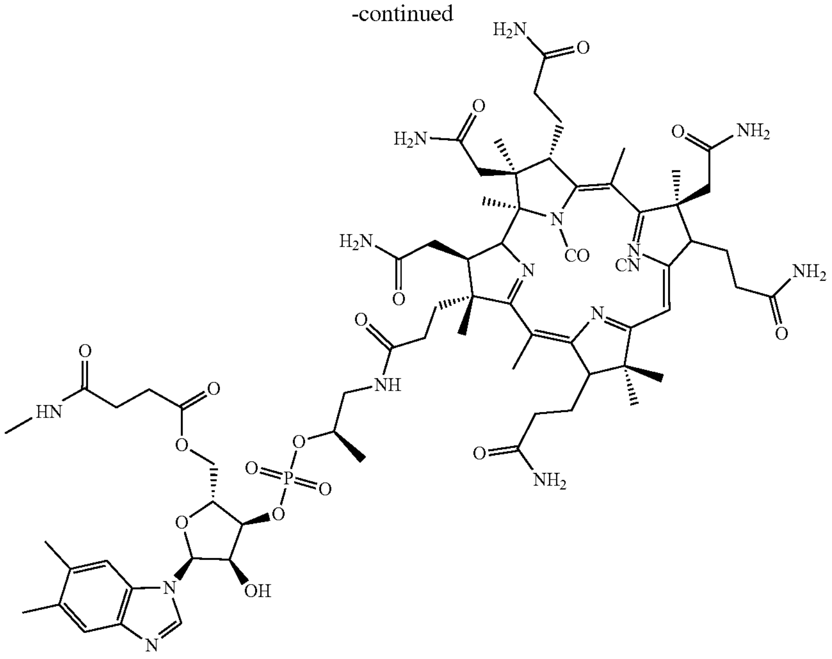

In one embodiment the target biological molecule is covalently attached to a dicarboxylic acid derivative of the primary (5') hydroxyl group of the ribose moiety of vitamin $B_{12}$.

In one embodiment the target molecule is bonded to the cobalt of vitamin $B_{12}$. Typically the bond is a cleavable dative covalent or ionic bond.

In one embodiment a 5'-O-glutaroyl derivative of vitamin $B_{12}$ is formed by acylation of vitamin $B_{12}$. Typically the acylation is with a reactive glutaric acid derivative, for example, the anhydride, to selectively convert the primary hydroxyl group (5'-OH) on the .alpha.-ribose moiety to a chemically reactive carboxyl group.

In one embodiment the vitamin $B_{12}$ acylated derivative is then subsequently reacted with a linker and/or spacer group to form a second derivative. Typically the second derivative in turn is reacted with the target molecule to form a the vitamin $B_{12}$-target conjugate. Further typically this conjugate is coupled to BtuG2.

In one embodiment the target molecule is attached via a reactive derivative of vitamin $B_{12}$, said derivative being modified at the primary (5') hydroxyl group on the ribose moiety to form a chemically reactive carboxyl group. Optionally the target molecule is attached to a further modified vitamin $B_{12}$, said further modification being the modification of the reactive carboxyl group on the ribose moiety into a mixed acid anhydride, acid halide, or activated ester functional group which is capable of being covalently linked to a target molecule.

In one embodiment a maleimide functionality can be attached to the ribose group allowing the conjugated $B_{12}$-derivative to interact with free cysteine residues on proteins.

In a preferred embodiment the vitamin $B_{12}$—target molecule conjugate is recovered, isolated and/or immobilised by association with BtuG2

In a second aspect of the invention there is provided a method of labelling, detecting, immobilisation and/or isolating at least one target molecule, said method including the step of forming at least one bond between vitamin $B_{12}$ and the target biological molecule and utilising the non-covalent affinity, coupling or binding between vitamin $B_{12}$ binding protein BtuG2, said interaction between BtuG2 and vitamin $B_{12}$ enabling the labelling, immobilisation, isolation and/or detection of the target molecule.

A method for preparing a conjugate of vitamin $B_{12}$ and a target molecule comprising the steps of: a) forming a derivative of vitamin $B_{12}$ by appending to the primary (5') hydroxyl group on the ribose moiety a chemically reactive group; b) optionally converting the chemically reactive group on the ribose moiety into a mixed acid anhydride, acid halide, activated ester, or maleimide functional group which is capable of being covalently linked to a target molecule; c) adding the vitamin $B_{12}$ derivative of step (a) or step (b) with the target molecule to form a conjugate of vitamin $B_{12}$ and the target molecule; and d) detecting, isolating, immobilising or recovering the conjugate by exposing the same to the vitamin $B_{12}$ binding protein BtuG2.

Specific embodiment of the invention are now described with reference to the following figures, wherein;

In the present invention, the linking of a fluorescent protein to a $B_{12}$-conjugate has been established, as evidenced by UV-Vis and mass spectral recordings. Conjugated fluorescent proteins with $B_{12}$ have then been observed to bind to BtuG2 that had been immobilised on a Ni-column.

A maleimide-$B_{12}$ conjugate has been shown to react with an antibody. The antibody complex has been shown to interact with BtuG2 through an ELISA system. This demonstrates the proof of principle that the BtuG2-$B_{12}$ binding system can be used in diagnostics.

Furthermore, bacterial extracellular vesicles (BEVs) or outer membrane vesicles (OMVs) generated by *Bacteroides thetaiotaomicron* (Bt) can provide it with the vit$B_{12}$ that is essential for its growth.

Figure 1:
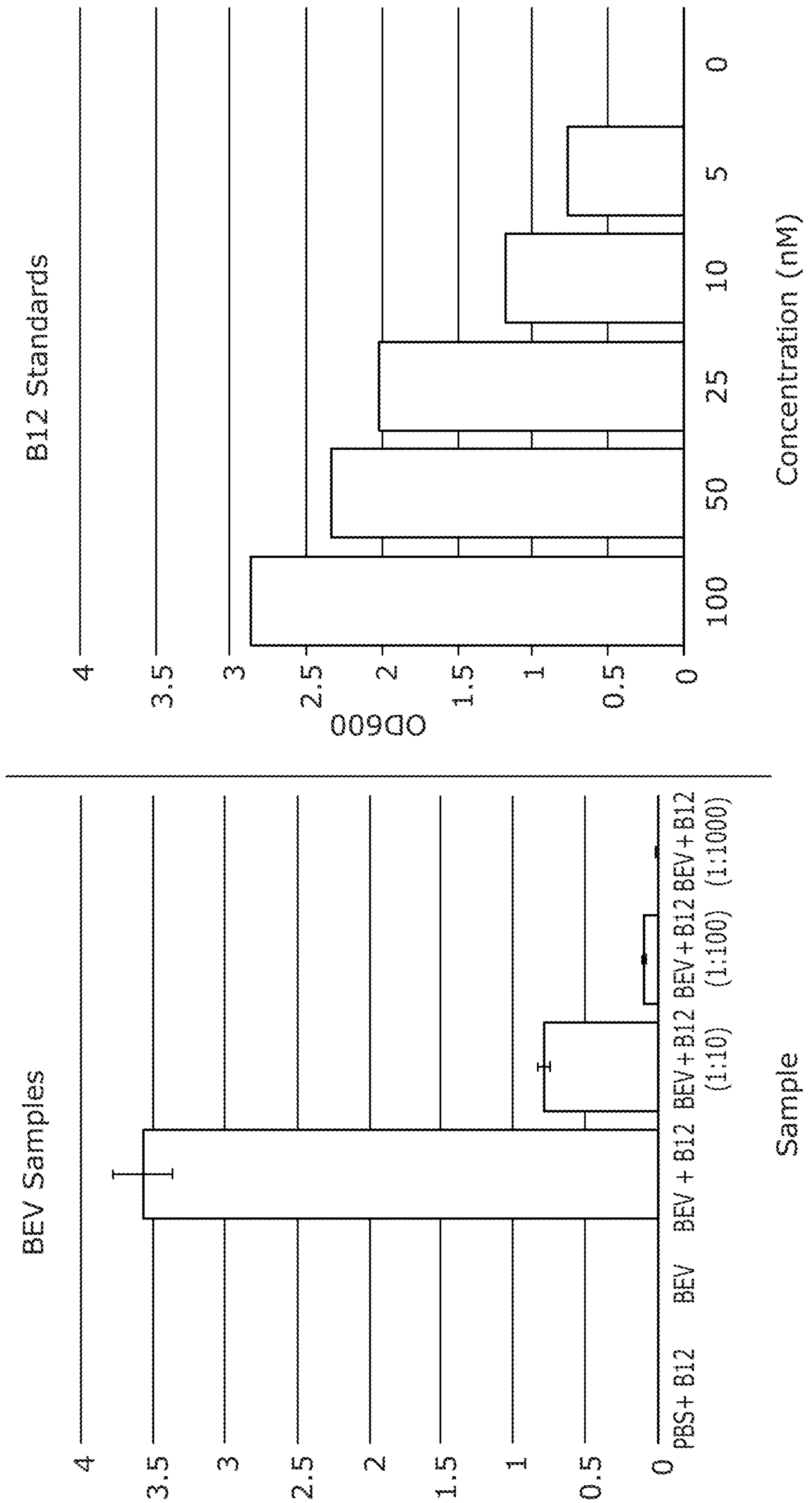
FIG. 1 shows graphs of the results of the growth of Bt being dependent upon vit$B_{12}$.
Figure 2:
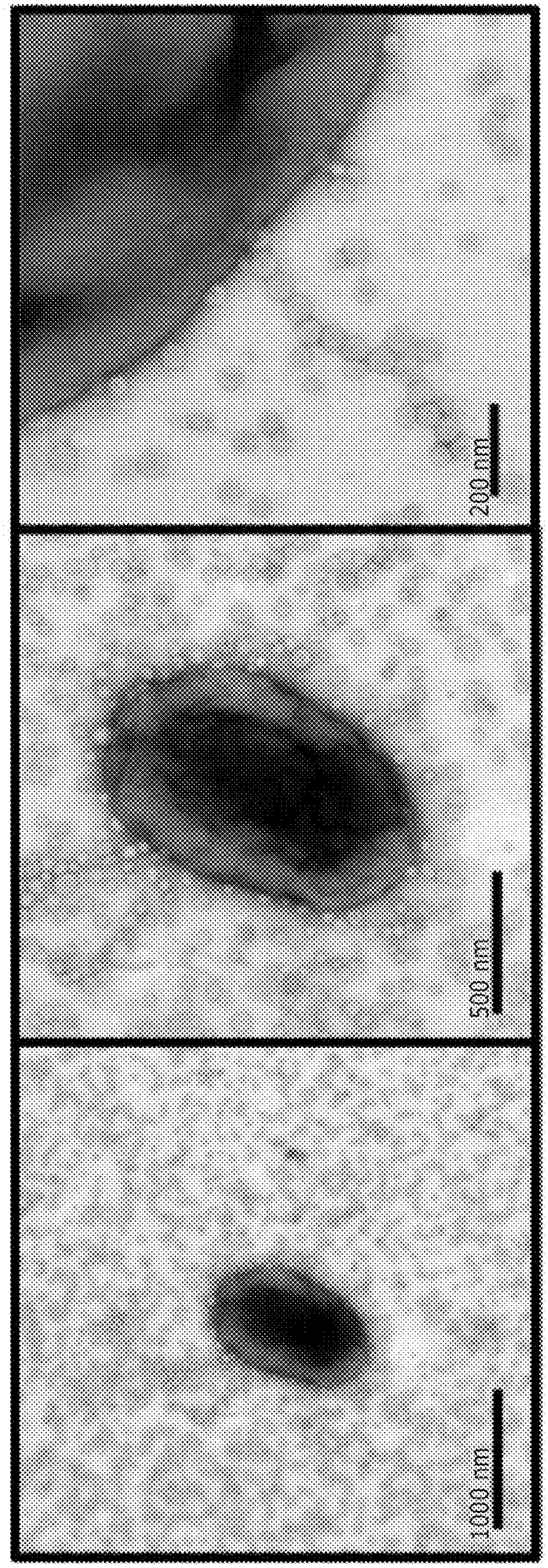
FIG. 2 shows electron micrographs of Bt BEVs.

The right panel of FIG. 1 shows that the growth of Bt is dependent upon vit$B_{12}$ with no growth possible in its absence (0 nM) with maximal growth at 100 nM vit$B_{12}$.

The left panel of FIG. 1 shows that BEVs incubated with 1 mM of vit$B_{12}$ can support the growth of Bt in vit$B_{12}$-deficient media. Less growth is seen with serial 10-fold dilutions of $B_{12}$-bound BEVs. By contrast and as controls, no growth is seen by adding 1 mM vit$B_{12}$ directly to the cultures or by adding BEVs alone with no bound vitB12.

BEVs bind vit$B_{12}$ in a form that retains its biological activity and can be utilised by parental bacterial cells for sustaining its growth.

Figure 3:
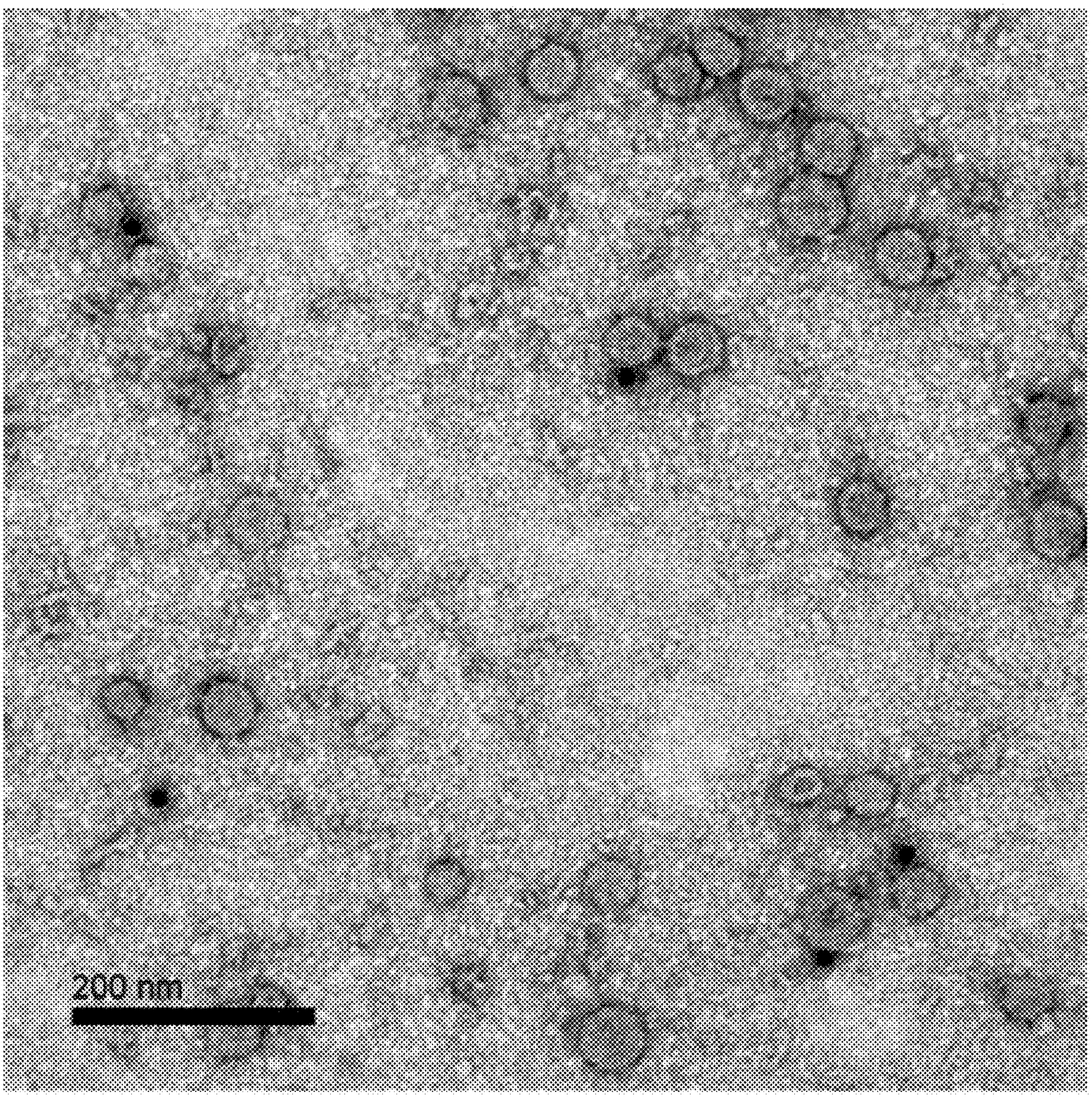
FIG. 3 shows gold label association with the OMVs

We have shown that a $B_{12}$-conjugated fluorescent protein binds to the Bt OMV via the $B_{12}$-binding protein BtuG2. Purified OMVs were mixed with the $B_{12}$-linked mCherry fluorescent protein—and the excess $B_{12}$ material washed away. The OMVs were then added to an EM grid and cross-reacted with a gold-labelled anti-mCherry antibody. The resulting EM picture in FIG. 3 shows that the gold label is associated with some of the OMVs.

The BtuG2 protein has extremely high affinity for $B_{12}$, somewhere in the femtomolar region. We believe that it is possible to exploit this tight interaction in the same way as the Biotin-avidin system. We have shown that it is possible to attach protein-linkers to vitamin $B_{12}$, allow vitamin $B_{12}$ to become attached to proteins that have the necessary exposed amino acid side chains. Vitamin $B_{12}$ containing either succinyl anhydride or PFP ester can react with exposed lysine residues, whilst $B_{12}$ with a maleimide functionality can react with exposed cysteine residues.

(a) We have shown that GFP labelled with $B_{12}$ will bind to BtuG2. The attachment is specific and strong.

(b) With Mologic, we have shown that a $B_{12}$-maleimide will bind to a lactate dehydrogenase antibody, allowing the complex to be used in an immunoassay. This provides the proof of principal that the B12-B12 binding protein system can be exploited in therapeutic assays and diagnostics in the same way as biotin-avidin.

The invention claimed is:

1. A composition comprising a vitamin $B_{12}$ binding protein BtuG2 and a vitamin $B_{12}$ conjugated to a target molecule;

wherein the BtuG2 is coupled via non-covalent affinity to the vitamin $B_{12}$ conjugated to the target molecule, and wherein the target molecule is any one of a biological molecule, peptide, protein, antibody or fluorescent protein.

2. The composition according to claim 1 wherein a bond between the vitamin $B_{12}$ conjugated to the target molecule is a covalent bond.

3. The composition according to claim 1 wherein when the target molecule is a biological molecule, the target molecule is bonded to a primary hydroxyl site of the ribose moiety of the vitamin $B_{12}$.

4. The composition according to claim 1 wherein the vitamin $B_{12}$ is not directly linked to the target molecule.

5. The composition according to claim 4 wherein the vitamin $B_{12}$ has an indirect linkage with the target molecule, and the indirect linkage is via a bridging molecule, linking elements or particles.

6. The composition according to claim 1 wherein the vitamin $B_{12}$ is attached to the target molecule by attachment of 5' hydroxyl of a ribose of a lower nucleotide loop of cobalamin.

7. The composition according to claim 1 wherein the vitamin $B_{12}$ is attached to the target molecule by attachment to a secondary alcohol of cobinamide.

8. The composition according to claim 1 wherein a linker compound is used to modify the vitamin $B_{12}$ with a linker compound or element.

9. The composition according to claim 1 wherein when the target molecule is a biological molecule, it is covalently attached to a dicarboxylic acid derivative of a primary (5') hydroxyl group of a ribose moiety of the vitamin $B_{12}$.

10. The composition according to claim 1 wherein the target molecule is bonded to a cobalt of the vitamin $B_{12}$.

11. The composition according to claim 1 wherein the vitamin $B_{12}$ is a 5'-O-glutaroyl derivative of vitamin $B_{12}$ and is formed by acylation of vitamin $B_{12}$.

12. The composition according to claim 1 wherein the target molecule is attached to the vitamin $B_{12}$ via a reactive derivative of vitamin $B_{12}$, said reactive derivative of vitamin $B_{12}$ being modified at a primary (5') hydroxyl group on a ribose moiety to form a chemically reactive carboxyl group.

13. The composition according to claim 12 wherein the target molecule is attached to a further modified vitamin $B_{12}$, said further modified vitamin $B_{12}$ being a modification of the reactive carboxyl group on the ribose moiety into a mixed acid anhydride, acid halide, or activated ester functional group which is capable of being covalently linked to the target molecule.

14. The composition according to claim 13 wherein a maleimide functionality can be attached to the ribose group to allow the conjugated further modified vitamin $B_{12}$ to interact with free cysteine residues on proteins.

15. The composition according to claim 1 for use in recovering, labelling, detection, immobilization and/or isolation of the target molecule or the vitamin B12-target molecule conjugate.

16. A method of labelling, detecting, immobilisation and/or isolating at least one target molecule, said method including the step of forming at least one bond between vitamin $B_{12}$ and the target molecule to form a vitamin $B_{12}$-target molecule conjugate, coupling the vitamin $B_{12}$-target molecule conjugate to vitamin $B_{12}$ binding protein BtuG2 via non-covalent affinity to form a complex of the vitamin $B_{12}$ binding protein BtuG2 and the vitamin $B_{12}$ conjugate to the target molecule, and using the coupling between BtuG2 and the vitamin $B_{12}$-target molecule conjugate to label, immobilise, isolate and/or detect the target molecule, and wherein the target molecule is any one of a biological molecule, peptide, protein, antibody or fluorescent protein.

17. The method according to claim 16, wherein the complex of the BtuG2 and the vitamin B12 conjugate to the target molecule is for use in an immunoassay.

18. The method according to claim 16 wherein the BtuG2 is immobilized on a Nio-column or on an affinity matrix.

* * * * *